United States Patent [19]

Pietsch et al.

[11] Patent Number: 4,643,732
[45] Date of Patent: Feb. 17, 1987

[54] HEART VALVE PROSTHESIS

[75] Inventors: Hanns Pietsch; Holger Kartheus, both of Hamburg; Helmut Reul, Düren, all of Fed. Rep. of Germany

[73] Assignee: Beiersdorf Aktiengesellschaft, Hamburg, Fed. Rep. of Germany

[21] Appl. No.: 789,587

[22] Filed: Oct. 21, 1985

[30] Foreign Application Priority Data

Nov. 17, 1984 [DE] Fed. Rep. of Germany ....... 3442088

[51] Int. Cl.⁴ .............................................. A61F 2/24
[52] U.S. Cl. ...................................................... 623/2
[58] Field of Search ................... 623/2; 604/323, 335, 604/350

[56] References Cited

U.S. PATENT DOCUMENTS 3,717,883  2/1973  Mosher ................................ 623/2
4,204,283  5/1980  Bellhouse .............................. 623/2
4,263,680  4/1981  Reul et al. ............................ 623/2

Primary Examiner—Richard J. Apley
Assistant Examiner—James Prizant
Attorney, Agent, or Firm—Sprung Horn Kramer & Woods

[57] ABSTRACT

A heart valve prosthesis with a valve housing in the form of a ring and a curved valve which is mounted within the housing and which is hinged to the valve ring by means of a flat flexible small lug which, if appropriate, is drawn in one region through a slot in the valve ring, is characterized in that the valve and the ring each consist of two rigidly joined halves fitting respectively onto or into each other, and the end portions of the small lug in the form of a short strip are embedded "sandwich"-like between the valve halves on one side and between the ring halves on the other side.

9 Claims, 6 Drawing Figures

HEART VALVE PROSTHESIS

The invention relates to a heart valve prosthesis, that is to say a prosthetic closing element for replacing the valves in a human heart, in particular the mitral valve and tricuspidal valve, with a valve housing in the form of a ring and a valve which is mounted within the housing, is convex in the upstream direction and is hinged by means of a flat flexible small lug which, if appropriate, is drawn in one region through a slot in the valve ring. In addition, the valve ring advantageously has an annular support face for the valve and is fixed by means of a conventional suture ring to the tissue. A comparable heart valve is the subject of German Patent Specification No. 2,815,756,* the disclosure content of which is incorporated herein by reference.

*which corresponds U.S. Pat. No. 4,263,680

The present invention represents a further development or improvement of the heart valve described in that patent specification.

An essential feature of the heart valve according to German Patent Specification No. 2,815,756 is the movable plastic hinge which, in the form of a small lug integrally joined to the cover (that is to say the valve)**, forms a strap which is drawn through a slot in the ring and fixed to the outside of the ring. At the point where the hinge is located, the ring and the cover are flattened (that is to say the circular surface is cut in the manner of a chord).

**"cover" and "valve" are synonymous words in this application

The main loading during functioning of the valve is on the plastic hinge which is stressed in bending. The plastics suitable for forming such a hinge must therefore have an excellent flexing fatigue strength and a low shore hardness, in order to withstand this continuous stress. Moreover, it has been found in long-term tests that torsional forces can arise in addition to the bending forces. These torsional forces stress the hinge from the edge and can be the cause of the hinge tearing from the side or of the cover being forced through the ring.

In the quoted German Patent Specification No. 2,815,756, it is described that the hinge-forming small lug should preferably be joined integrally to the cover. This "integrality" is obtained by coating the cover completely from both sides with plastic. At the point where the hinge is located, the coating extends in the form of a strap beyond the cover. The advantages of this heart valve are that it has a hinged joint which, apart from its functional reliability, has no adverse effects on the blood flow at all. This construction provides soft flow control both in the open position and in the closed position, and thrombus-generating dead water zones, harmful friction and high shear stresses damaging the blood are avoided.

As a result of the design of the hinge in the form of a flat small lug, there are substantially no flow obstacles during the inflow phase, whereas a fairly severe restriction of the flow cross-section arises in the previously known heart valves because of the space-demanding design of the hinged joint. Moreover, the closing element according to German Patent Specification No. 2,815,756 has a relatively small overall height, and the height of the valve ring can correspond to the height of the valve shaped as a segment of a sphere. The hinged joint in the form of the flat small lug then does not require any increase in the overall height, since the suture ring can be fitted to the side of the hinge.

The advantages resulting from the hinge design described are further reinforced by the fact that the valve is shaped as a shell-like element in the form of a segment of a sphere. The shaping of the valve as a segment of a sphere results on the one hand in an increase in strength (pressure differences of up to 300 mm Hg can arise in the closed state) and, on the other hand, has functional reasons, which are explained below, taking the mitral valve as an example:

When the chamber of the heart fills, the mitral valve opens very quickly and the blood jet entering the chamber impinges on the chamber tip, spreads sideways and upwards behind the two natural mitral sails and simultaneously creates in the expanding heart chamber a vigorous circular vortex which holds the two sails in a stable position. When the inflow slows down, the pressure difference on the two sides of the sails causes a movement in the direction of the closed position. As a result, the mitral valve is already closed before the chamber contraction and hence the outflow phase begin. This mode of functioning is safeguarded by the construction of the hinge. It has been found that the vortex created behind the shell effects closure of the valve before the chamber contraction begins. The diameter of the segment of a sphere is here of the order of magnitude of the vortex diameter, so that the shell adapts itself harmoniously to the physiologically determined flow pattern.

The further mode of functioning of this valve type is described in detail in German Patent Specification No. 2,815,756.

However, the valve described above has the following disadvantages:

1. The plastic forming the small lug must have excellent adhesion to the metal cover, and this is not the case with the polyurethanes preferably used. Although the epoxide used as an adhesion promoter improves adhesion, the latter is not sufficient to prevent detachment of the coating in continuous functioning.
2. The cover is coated preferably by dip-coating. In this case, thin areas are formed at the edges of the cover, and these areas tear easily, particularly where the strap is attached.
3. The strap is joined to the ring via tightened threads which run in the outer groove of the ring, or by adhesive bonding in this groove-like recess. However, the strength of this joint is inadequate, as has been found in continuous operation. The cover can become loose and then assume a transverse position in the ring or can be completely drawn out.
4. The cover in the form of a segment of a sphere has a shape which, on its cut side, is arcuate towards the hinge, so that the hinge-forming small lug is also curved in its transverse direction. This causes increased loading at its edges, so that notched tears can easily start from the edge.

It was therefore the object of the invention to preserve the excellent rheological properties of the heart valve as such, but to eliminate the disadvantages described.

According to the invention, this object is achieved by a heart valve prosthesis with a valve housing in the form of a ring and a curved valve which is mounted within the housing and which is hinged to the valve ring by means of a flat flexible small lug, which, if appropriate, is drawn in one region through a slot in the valve ring, which prosthesis is characterised in that the valve and the ring each consist of two rigidly joined halves fitting respectively onto or into each other, and the end portions of the small lug in the form of a short strip are embedded "sandwich"-like between the valve halves on one side and between the ring halves of the other side.

The hinge-forming strap is thus likewise integrally joined to the cover, but not from the outside as in the heart valve according to German Patent Specification No. 2,815,756, but by insertion of a strip of textile material or preferably flexible plastic between two cover halves in the form of a "sandwich".

When the heart valve according to the invention is produced, the hinge-forming strap is placed with one of its ends between the two cover halves in such a way that about 5-10 mm of the strip project on the flattened side of the cover and about 60-80% of its length is within the cover. The two cover parts are then joined to the strip inserted in between, either by welding, adhesive bonding, screwing or by riveting, preferably by ultrasonic welding. The cover is joined to the ring by drawing the strip, projecting from the flattened side of the cover, preferably through a small slot in the inner part of the ring, until the cover no longer has any play, slipping the outer part of the ring over this and then joining the two parts of the ring, preferably by welding. The strip end can also be inserted directly between the two ring halves and welded in. In this way, the two end portions of the strip forming the hinge are rigidly and durably anchored in the cover and in the ring.

The ring and cover halves are preferably produced by injection-moulding. Suitable materials for this are thermoplastics which are non-toxic, non-degradable enzymatically and compatible with blood. The mechanical properties demanded from the material are high stiffness and also good fracture strength and bending strength. In addition, the material should be hydrolytically stable and not contain any toxic auxiliaries.

Examples of substances which meet these requirements are high-molecular low-pressure polyethylenes produced by the Ziegler-Natta process. Polycarbonate, polyoxymethylene and polyether-sulphone are also outstandingly suitable, the first-mentioned being particularly preferred.

In a further special embodiment of the heart valve, the flexible strap is attached to the inner ring part, that is to say is formed integrally with the latter, which can be accomplished, for example, by moulding it on as it is produced, and its free end is embedded "sandwich"-like between the two valve halves.

In this case, the inner part of the ring does not consist of the abovementioned thermoplastics, but of the flexible material of the strap.

To relieve the hinge in the sense of the disadvantages listed above under item 4, the construction of the cover, in a particularly preferred embodiment, was modified by comparison with German Patent Specification No. 2,815,756, in such a way that the curved cover is flattened towards the hinge, so that the hinge-forming small lug lies in the plane of the axis of rotation. As can be seen from FIG. 4, this flattening is advantageously of such a shape that its peripheral line forms approximately a semicircle above the hinge axis as the base.

The scrap or the hinge is the critical part of the heart valve prosthesis. The demands to be met by the material are: excellent biological tolerance, no toxicity and not even any toxic constituents subject to elution, hydrolytic stability, no enzymatic degradability, excellent flexibility, extremely high fatigue strength under alternate bending with a shore A hardness of 20 to 70 and rubber-elastic properties at 37° C. and below.

Substances with rubber-elastic properties at 37° C. or below are also called elastomers. These are (according to ELIAS in "Makromolekule [Macromolecules]", Hü thig and Wepf Verlag Basel, Heidelber 1971, page 22) macromolecular substances having moduli of elasticity of $10^6$–$10^7$ dynes/cm$^2$ and a reversible elongation of 200 to 1000% (see also B. Vollmert, Grundriss der makromolekularen Chemie [Principles of macromolecular chemistry], Springer Verlag, Berlin, Göttingen, Heidelberg, 1962, pages 397 et seq., where the molecular processes of elastic deformation are extensively described with illustrations).

Amongst the usual elastomers, those particularly suitable for the use described here are the segmented polyether-urethanes, polyether-ureas, polydimethylsiloxanes, copolymers of ethylene and propylene (EPM), copolymers of ethylene, propylene and a diene (EPDM) or a vinylidene fluoride/hexafluoropropylene copolymer (for example Viton A ®, Du Pont). Polydimethylsiloxane and EPDM have proved particularly suitable. The common feature of all these elastomers is a glass temperature below 0° C. (definition of this term in, for example, J. Brandrup, E. H. Immergut, Polymer Handbook, Interscience Publishers, New York, London, Sydney, 1966, III, 61 et seq.).

As already mentioned, the strap is subjected to high alternating bending and torsional stresses in the use of the heart valves. In particular the torsional stress involves the risk of lateral tearing of the strap. Its edges must therefore be free of compressions and irregularities, such as may arise, for example, by cutting with a knife, scalpel or scissors. Advantageously, the lateral edges of the strap are therefore rounded, and preferably even somewhat thickened as compared with the remaining thickness of the strip. The rounded edges are produced either by melt-cutting (hot wire or laser beam cut) when thermoplastic elastomers are used or by appropriate moulding when silicone rubbers are used.

The thickness of the hinge-forming small lug is 0.1-2.0 mm, preferably 0.3-0.8 mm.

The heart valve prosthesis according to the invention is described below by way of example, by reference to the figures.

On assembly of the valve, the hinge-forming strap g (see FIG. 5) is drawn through this slot and the outer ring part is then slipped over the inner ring part. The strap emerging from the slot is thus clamped in between the outer ring part and the inner ring part. The outer ring part and inner ring part with the clamped strap are then adhesively bonded and/or welded to one another and the projecting part of the strap is cut off short.

Figure 1:
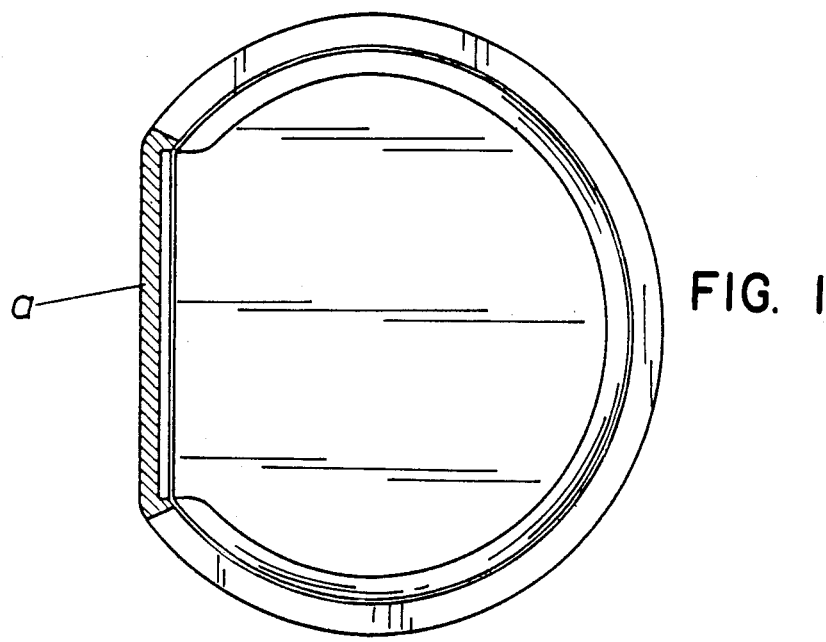
FIG. 1 shows the ring in plan view with the chordlike cut a. This forms the hinge axis.
Figure 2:
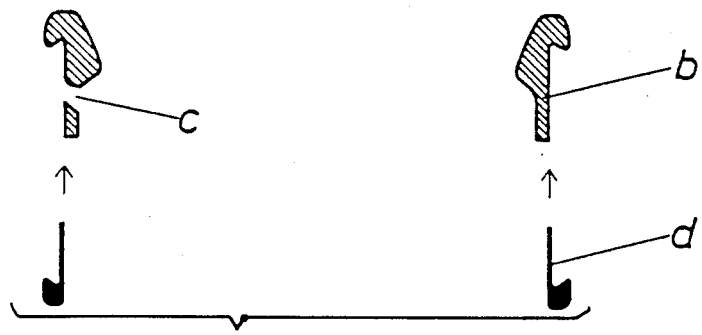
FIG. 2 shows a cross-section of the ring consisting of an outer ring part d and an inner ring part b. On the flattened side a, the inner ring part has a slot c.
Figure 3:
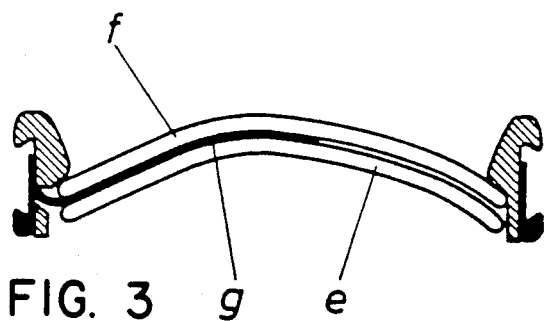

FIG. 3 shows the complete valve without suture ring in cross-section, namely the upper cover part f, the lower cover part e and, in between, the hinge-forming strap g which is clamped in by the two ring parts b and d at the location of the slot c.

Figure 4:
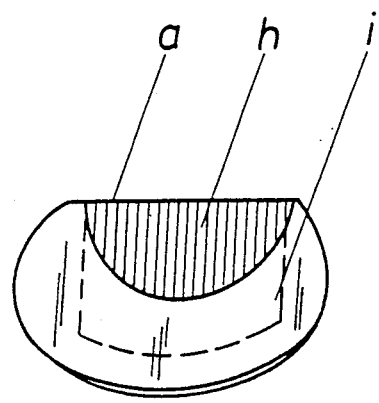

FIG. 4 shows a cover half shell e or f with the chordlike cut a and the arcuate flattening h and a recess i for the hinge strap to be inserted.

Figure 5:
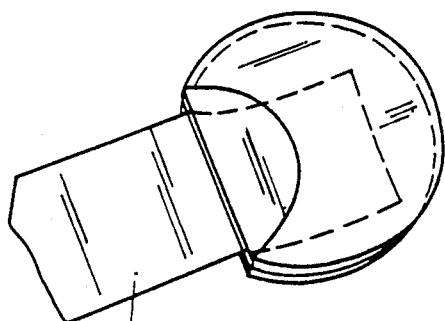
Figure 6:
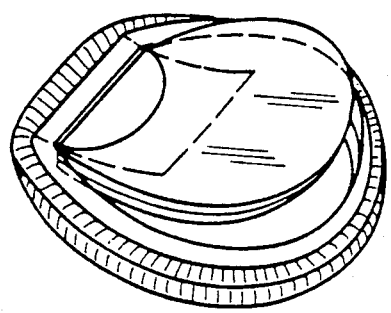

FIG. 5 shows the two assembled cover halves e and f with the inserted hinge strap, viewed from above corresponding to FIG. 6.

FIG. 6 shows the finished heart valve prosthesis with a textile suture ring, in the opened state.

We claim:

1. A heart valve prosthesis consisting of a valve housing in the form of a ring and a curved valve which is mounted within the housing and which is hinged to the valve ring by means of a flat flexible small lug, is characterised in that the valve and the ring each consist of two rigidly joined halves fitting respectively onto or into each other and the end portions of the small lug in the form of a short strip are embedded "sandwich"-like between the valve halves on one side and between the ring halves on the other side.

2. A heart valve prosthesis with a valve housing in the form of a ring and a curved valve which is mounted within the housing and which is hinged to the valve ring by means of a flat flexible small lug, characterised in that the valve and the ring each consist of two rigidly joined halves fitting respectively onto or into each other, and the small lug is formed integrally with the inner ring half and its free end is embedded "sandwich"-like between the two valve halves.

3. A heart valve prosthesis according to claims 1 or 2, characterised in that the curved valve is flattened towards the hinge.

4. A heart valve prosthesis according to claims 1 or 2 characterised in that the small lug forming the hinge has a thickness of 0.1 to 2.0 mm and round contours on the side edges.

5. A heart valve prosthesis according to claims 1 or 2 characterised in that the small lug forming the hinge, or the small lug and the inner ring half formed integrally with it, consists of rubber-elastic polyether-urethanes, polyether-ureas, polyether-urethane/silicone hybrid elastomers, ethylene/propylene copolymers (EPM), ethylene/propylene/diene copolymers (EPDM) or polydimethylsiloxanes.

6. A heart valve prosthesis according to claims 1 or 2, characterised in that the small lug forming the hinge, or the small lug and the inner ring half formed integrally with it, consists of polydimethylsiloxane (silicone rubber) or a copolymer of ethylene, propylene and a diene (EPDM).

7. A heart valve prosthesis according to claims 1 or 2, characterised in that the ring and valve halves of the outer ring half and the valve halves respectively consist of a thermoplastic such as low-pressure polyethylene, polycarbonate, polyoxymethylene or polyether-sulphone and have preferably been produced by the injection-moulding process.

8. A heart valve prosthesis according to claims 1 or 2, characterised in that the valve and ring halves are each adhesively bonded or welded to one another and to the small lug.

9. A heart valve prosthesis according to claim 8, characterised in that the components are welded together ultrasonically.

* * * * *